United States Patent [19]
Ruff et al.

[11] Patent Number: 4,844,306
[45] Date of Patent: Jul. 4, 1989

[54] BLOOD PRESSURE CUFF HARNESS

[75] Inventors: Gray E. Ruff, Hillsboro; Jack Millay, Beaverton, both of Oreg.

[73] Assignee: SpaceLabs, Inc., Bothell, Wash.

[21] Appl. No.: 104,322

[22] Filed: Oct. 2, 1987

[51] Int. Cl.$^4$ .............................................. A51B 5/02
[52] U.S. Cl. ..................................... 224/202; 128/77; 224/258
[58] Field of Search .............. 224/208, 204, 205, 242, 224/246, 247, 252, 254, 257, 258, 264, 269, 202; 128/77, 689, 900; 623/57, 58

[56] References Cited

U.S. PATENT DOCUMENTS

| | | | |
|---|---|---|---|
| 396,061 | 1/1889 | Allward | 623/58 |
| 2,408,880 | 10/1946 | Rebers | 623/58 |
| 4,598,703 | 7/1986 | Lindemann | 128/77 |

FOREIGN PATENT DOCUMENTS

| | | | |
|---|---|---|---|
| 442017 | 4/1912 | France | 224/202 |
| 1422146 | 1/1976 | United Kingdom | 224/202 |

*Primary Examiner*—Renee S. Luebke
*Attorney, Agent, or Firm*—Seed and Berry

[57] ABSTRACT

A harness is provided for holding a blood pressure cuff in the correct position on the arm when being worn for extended periods of time. The harness has a support member that attaches by clasps directly to the cuff on the person's arm. The support member extends from the cuff to the shoulder region of the user so that the weight of the cuff is carried by the shoulder rather than by the arm through contact pressure from the cuff itself. The support member prevents slippage or rotation of the cuff throughout the monitoring period. A strap is provided that attaches to the support member at the shoulder region and runs under the other arm of the user to hold the support member in the correct position.

8 Claims, 2 Drawing Sheets

BLOOD PRESSURE CUFF HARNESS

TECHNICAL FIELD

This invention relates to a medical support harness, and more particularly, to a harness for holding a blood pressure cuff in the proper position on the arm for extended periods.

BACKGROUND ART

The blood pressure of a person is presently used as an important factor in determining the overall health of an individual. Further, it is often important either to record the blood pressure of an individual at a given time during the day or to record the variations in blood pressure throughout the day. Presently, blood pressure testing devices are available that are worn for extended periods, such as 24 to 48 hours. The blood pressure is taken and recorded on a regular basis throughout this extended period. In a typical blood pressure monitoring program, the patient wears a blood pressure cuff the entire monitoring period. An electronic system tests and records the blood pressure of the person every 20 or so minutes throughout the monitoring period. A small air pressure pump, electronic control, sensors and recorder are provided which pump up the cuff and record the blood pressure at the selected timed intervals.

The cuff often has sensors to perform the function of determining the blood pressure. It is therefore important that the cuff not rotate excessively so that the sensors and bladder are in the correct position to obtain an accurate reading of the blood pressure.

The individual wearing the blood pressure cuff is required to wear the cuff for the entire test period and keep it in the correct position so that the blood pressure readings are accurate. Unfortunately, during this extended period of 24 to 48 hours, the blood pressure cuff tends to slip down or move from its correct position on the arm. This is because during those intervals when a blood pressure reading is not being taken, the blood pressure cuff is deflated and fits more loosely around the arm.

It the cuff is worn for an extended period of time, it is not inflated most of the time. The only force acting to prevent the cuff from moving is the friction from contact with the arm and the full weight of the cuff is borne by the arm. Further, the tightness of the fit depends upon the circumference of the patient's arm. As the person flexes and stretches his arm, the circumference and shape of the arm will change and thus the fit of the cuff around the arm will vary throughout the day.

One solution is to wrap the cuff tightly around the arm when the cuff is not inflated. This is not satisfactory as it creates discomfort and the tightness of the fit will change as the person moves his arm. Further, the weight of the cuff is still borne solely by the arm in the general region of where the measurement is taken.

The problem of movement of the blood pressure cuff is particularly acute in overweight people. It is not uncommon for a person, particularly if he is overweight, to have a somewhat larger circumference at the top of his arm towards the shoulder than the circumference towards the elbow, gradually decreasing from the shoulder down. Thus, the arm of the person is in the shape of an inverted cone. To deal with this, the blood pressure cuff for such an individual may be made in the shape of an inverted cone so as to more closely fit the contour of the arm. However, this does not solve the problem of downward slipping or rotating of the cuff. The result is that an inverted cone (the arm) has another inverted cone (the cuff) wrapped around it, which will easily slip downward.

Another solution is to tape the cuff in position on the arm. While this does provide some additional support, it is not a satisfactory solution. The tape may contain a skin irritant which causes great discomfort to the skin while being worn. Further, when the tape is removed, there is discomfort from the pulling of hairs on the person's arms. Further, the tape often becomes loose if the person is moving his arm frequently or if the person has an oily skin or begins to perspire.

DISCLOSURE OF THE INVENTION

It is therefore an object of the invention to provide a harness for holding a blood pressure cuff in the correct position for extended periods of time.

It is a further object of the invention to transfer the weight of the blood pressure cuff to a region different from the location where the measurements are being taken.

It is a further object of the invention to provide a support for the blood pressure cuff having an elastic member extending to the shoulder, with the weight of the cuff being carried in part by the shoulder of the person and a strap extending from that shoulder to under the other arm of the user.

These and other objects of the invention are provided by attaching a harness to a blood pressure cuff and extending the harness to the shoulder of the user so that some or all of the weight of the cuff is carried by the shoulder. A strap is attached to the harness in the shoulder region of the user and goes under the other arm of the user to hold that part of the harness in the correct position on the shoulder of the user. Clasps are connected to the end of the harness support member which can be removably attached to the blood pressure cuff. When wearing the harness, the user places one arm through the strap and extends the strap across his back to the shoulder of the other arm for holding the cuff support member in the correct position on the shoulder. The cuff support member extends from this shoulder down the arm and attaches to the blood pressure cuff. In the alternative, the user places his head and arm through the strap so that one of the straps extends across the front of the user and the other strap extends across the back of the user to the shoulder region for holding the support member in the correct position at the shoulder region. Either the strap or the support member may be made of nonelastic material if desired.

BEST MODE FOR CARRYING OUT THE INVENTION

Figure 1:
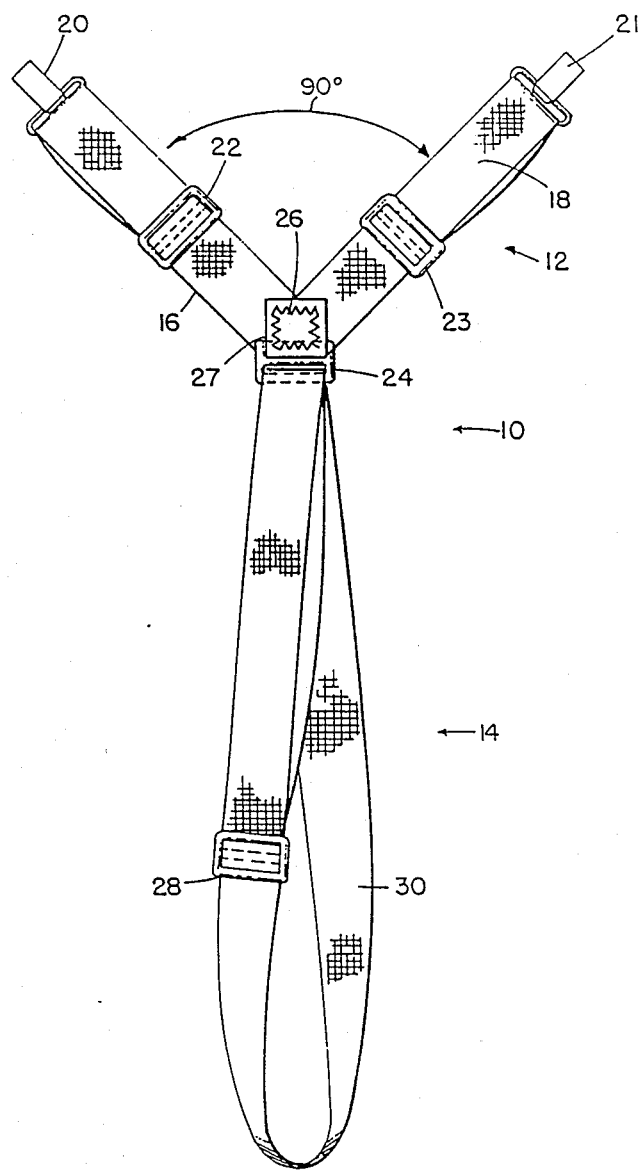
FIG. 1 is a front elevational view of the harness in a flat position when not in use.
Figure 2:
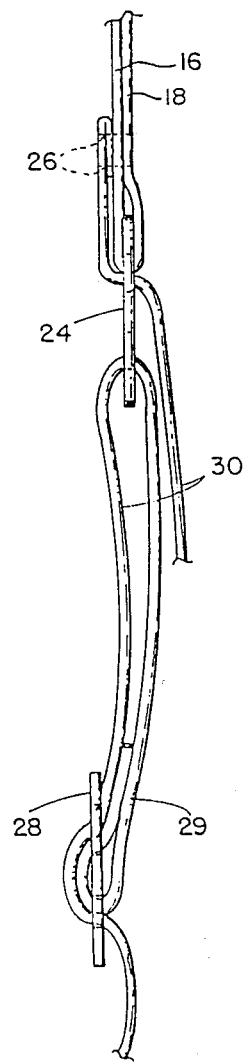
FIG. 2 is a side elevational view of a portion of the harness.

The harness 10, as illustrated in FIGS. 1 and 2, includes a cuff support member 12 and a shoulder support member 14. The cuff support member 12 has two support arms 16 and 18, respectively, extending at 90° angles with respect to each other. The support arms 16, 18 of the cuff support member 12 are sewn at junction 26 such that the two support arms 16, 18 extend away from the fastener at a 90° angle with respect to each other. A retaining tab 27 is sewn with the support arms 16, 18, and it is looped through the fastener to connect the cuff support member 12 to the shoulder support member 14. Support arms 16 and 18 are formed from a one-piece elastic member. The member is passed through an opening in a fastener 24 and sewn at a midpoint junction 26 to create arms 16 and 18 extending at a 90° angle with respect to each other. In a preferred embodiment, the single support member is 22 inches long.

The support arms 16, 18 are looped and connected into respective adjustment sliders 22, 23 to allow the length of the support arms 16, 18 to be adjusted. Clasps 20 and 21 are connected in the respective loops of each of the support arms 16, 18. When the clasps 20, 21 are opened, a portion of the blood pressure cuff may be inserted therein and the clasps closed to provide a firm attachment to the blood pressure cuff by the clasp. The clasp may be easily opened for removal of the blood pressure cuff. Clasps of this type are well known and are often used in suspenders. Other removable attachment devices, such as Velcro TM, buttons, etc., could be used if desired.

The shoulder support member 14 includes an elastic strap 30 having one end looped around a fastener 24. A slider 28 in the looped end of the strap 30 permits easy adjustment of the length of the strap 30. The other end of the strap 30 is sewn into the same junction 26 with the support arms 16, 18. The strap 30 is formed with a one-half twist to provide complete contact and comfort as it extends from the shoulder to under the other arm.

Figures 3A, 3B:
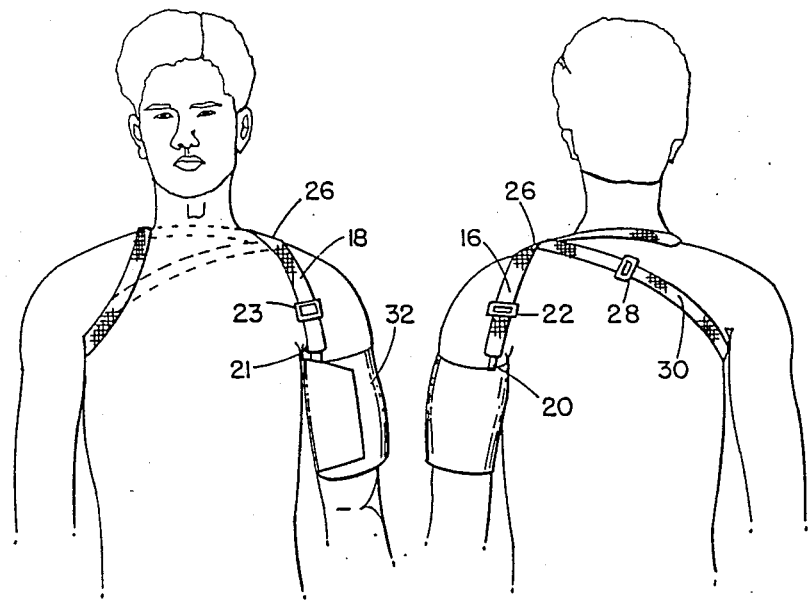
FIGS. 3A and 3B are a front and back elevational view, respectively, of a person wearing the harness.

FIGS. 3A and 3B illustrate a person wearing the harness attached to a blood pressure cuff. The blood pressure cuff 32 is wrapped around the arm of the person in a manner well known in the art. Clasp 21 is attached to the front of the blood pressure cuff. Support arm 18 is connected to clasp 21 and extends up the front of the arm to the shoulder region of the user. Similarly, support arm 16 is attached by clasp 20 tot he rear portion of the blood pressure cuff, as shown in FIG. 3B. Support arm 16 extends from the blood pressure cuff up the back of the arm to the shoulder region of the user. The two support arms are joined together at junction 26 above the blood pressure cuff on the shoulder region of the user. In this way, the weight of the blood pressure cuff is supported through the straps by the shoulder of the person. The blood pressure cuff does not slip down the arm towards the elbow of the user even when worn for extended periods. Further, the support arms prevent rotation of the cuff. When periodic readings are taken throughout the extended period, the blood pressure cuff is held in the correct position for each of the readings. The blood pressure cuff may now be wrapped less tightly around the person's arm. The inward pressure of the cuff on the arm need not support the cuff to keep it from slipping downward or rotating. Flexing or extending the arm will not affect the position of the cuff.

Strap 30 is provided for holding the support arms in the correct position on the shoulder of the user. This strap 30 is connected to the junction 26 and through a fastener to the cuff support member 12. Strap 30 extends from the shoulder region above the blood pressure cuff across the back of the person and under the arm of the individual, as in FIGS. 3A and 3B. In this way, the cuff support member 12 is held in the proper and comfortable position in the shoulder region of the user for extended periods of time.

In the alternative, the strap 30 may be worn by the user with a portion of the strap extending across the chest and a portion across the back, with the loop extending under the arm. In certain circumstances, this may provide more comfort and better positioning than extending both straps across the back.

The harness is preferably made of an elastic material, with straps 30, 16 and 18 being elastic. This provides comfort for the user. The user may continue his normal activities through the extended monitoring period and have full ability to move his limbs and body without displacing the blood pressure cuff.

In the alternative, the harness may be made of a nonelastic material such as cloth or leather, with the strap being elastic, or vice versa, with the strap being made of cloth or leather and the support member being made of elastic.

In the preferred embodiment, the cuff support member 12 has two support arms 16, 18; however, the cuff support member 12 could be comprised of a single support arm properly positioned to keep the blood pressure cuff in the correct position throughout the monitoring period. Further, a single extending support member with an inverted V connection or other type of positioning support may also be used. Use of the shoulder support member 14 is preferred; however, it is also possible to use the cuff support member 12 without shoulder support member 14.

We claim:

1. A blood pressure cuff support harness comprising:
an elastic support member attachable to a blood pressure cuff on a user, said elastic support member extending from said blood pressure cuff to a shoulder region adjacent said arm for supporting the weight of said blood pressure cuff from said shoulder region while permitting relative movement between said support member and said shoulder region;
a shoulder member positioned on said shoulder region, said shoulder member coupled to said elastic support member;
an elastic strap coupled to said shoulder member at said shoulder region, said strap extending from said shoulder member, across the torso, and underneath the other arm of said user.

2. The harness of claim 1 wherein said shoulder member includes a rigid fastener.

3. The harness of claim 1 wherein said elastic strap is sewn into said elastic support member.

4. The harness of claim 1 wherein said elastic support member is a single elastic member having a front support arm and back support arm, said front support arm extending from a position on the front of said user's arm to said shoulder region and said back support arm extending from a position on the back of said user's arm to said shoulder region, said single elastic strap extending through a rigid fastener at said shoulder region.

5. The harness of claim 4 wherein said front support arm and said back support arm are sewn at 90 degrees with respect to each other at each shoulder region.

6. The harness of claim 4 wherein a first end of said strap is sewn into said single elastic support member and a second end of said strap is sewn into itself.

7. A blood pressure cuff support harness comprising:
an elastic support member consisting of a single strap attachable at a first end thereof to a front of a blood pressure cuff and at a second end thereof to a back of said blood pressure cuff, said elastic support member extending from a front position on the front of a user's arm, over a shoulder region of said user, and to a rear position of said user's arm causing the weight of said blood pressure cuff to be borne by said shoulder region;

a fastener positioned at said shoulder region through which said elastic support member extends;

a single elastic strap for holding said fastener in position on said shoulder region coupled directly to said elastic support member extending from said shoulder region, through said fastener, under the other arm of said user, through said fastener and sewn into itself.

8. The blood pressure cuff support harness of claim 7 wherein said first end of a said elastic support member is sewn at a 90 degree angle with respect to said second end.

* * * * *